United States Patent [19]

DiNinno et al.

[11] Patent Number: 5,334,590
[45] Date of Patent: Aug. 2, 1994

[54] MRSA ACTIVE 2-PHENYL-CARBAPENEMS

[75] Inventors: Frank DiNinno, Old Bridge; Ravindra N. Guthikonda, Edison, both of N.J.

[73] Assignee: Merck & Co., Inc., Rahway, N.J.

[21] Appl. No.: 92,770

[22] Filed: Jul. 16, 1993

Related U.S. Application Data

[63] Continuation of Ser. No. 777,949, Oct. 17, 1991, abandoned.

[51] Int. Cl.$^5$ .............. C07D 487/00; A01N 43/00; A61K 31/395
[52] U.S. Cl. ..................... 514/210; 540/302
[58] Field of Search .......... 540/302; 514/210

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,729,993 | 3/1988 | Christensen et al. | . |
| 4,775,669 | 10/1988 | Cama et al. | . |
| 4,962,101 | 10/1990 | DiNinno et al. | . |
| 4,978,659 | 8/1989 | DiNinno et al. | . |
| 5,004,729 | 4/1991 | Salzmann et al. | . |
| 4,978,659 | 12/1990 | Salzmann et al. | . |
| 5,006,519 | 4/1991 | DiNinno et al. | . |
| 5,011,832 | 4/1991 | Salzmann et al. | . |
| 5,025,006 | 6/1991 | Salzmann et al. | . |
| 5,025,007 | 6/1991 | Greenlee et al. | . |
| 5,025,008 | 6/1991 | DiNinno et al. | . |
| 5,032,587 | 7/1991 | DiNinno et al. | . |
| 5,034,384 | 7/1991 | Greenlee et al. | . |
| 5,034,385 | 7/1991 | DiNinno et al. | . |
| 5,037,820 | 8/1991 | DiNinno et al. | . |

FOREIGN PATENT DOCUMENTS

| | | | |
|---|---|---|---|
| 0010316 | 4/1980 | European Pat. Off. | . |
| 277743 | 8/1988 | European Pat. Off. | 540/302 |

OTHER PUBLICATIONS

L. D. Cama et al., Total Synthesis of Thienamycin Analogs-III Tetrahedron 39, 2531 (1983).
R. N. Guthikonda et al., Structure Activity Relationship in the 2-Arylcarbapenem Series, J. Med. Chem., 30, 871 (1987).

*Primary Examiner*—James H. Reamer
*Assistant Examiner*—Rebecca Cook
*Attorney, Agent, or Firm*—Richard C. Billups; Mark R. Daniel

[57] ABSTRACT

Carbapenems of the formula

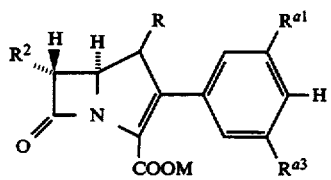

are useful antibacterial agents.

12 Claims, No Drawings

MRSA ACTIVE 2-PHENYL-CARBAPENEMS

CROSS REFERENCE TO RELATED APPLICATIONS

This Application is a Continuation of U.S. patent application Ser. No. 07/777,949 filed on Oct. 17, 1991, and now abandoned, priority of which is claimed hereunder.

BACKGROUND OF THE INVENTION

The present invention relates to antibacterial agents of the carbapenem class, in which the 2-position sidechain is characterized by a phenyl moiety, substituted by various substituents, as described in more detail further below.

Thienamycin was an early carbapenem antibacterial agent having a broad spectrum; it has the following formula:

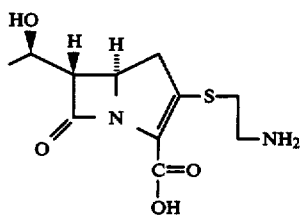

Later, N-formimidoyl thienamycin was discovered; it has the formula:

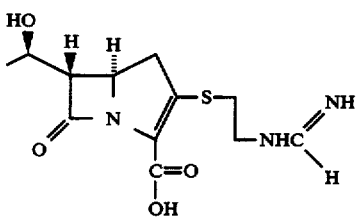

The 2-phenyl-carbapenems of the present invention are not necessarily of interest for a broad antibacterial spectrum such as that of thienamycin or N-formimidoyl thienamycin. Rather, their spectrum of activity of primary interest is to gram positive microorganisms, especially methicillin resistant *Staphylococcus aureus* (MRSA), methicillin resistant *Staphylococcus epidermidis* (MRSE), and methicillin resistant coagulase negative *Staphylococci* (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

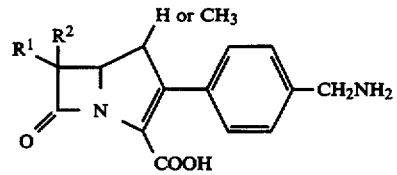

However, there is no description or suggestion of a phenyl 2-substituent providing suprisingly better anti-MRSA/MRCNS activity as do the compounds of the present invention.

U.S. Pat. No. 4,978,659 describes a particular class of compounds of the formula:

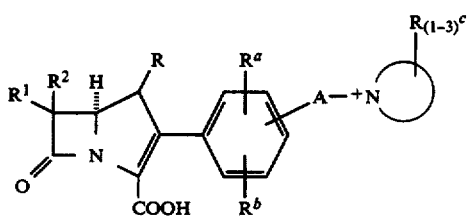

but this limited teaching in no way suggests the surprisingly better anti-MRSA/MRCNS activity.

SUMMARY OF INVENTION

The present invention provides novel carbapenem compounds of the formula:

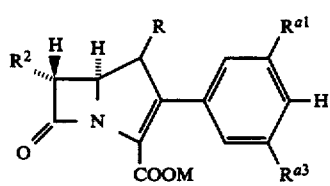

wherein:

R is H or CH$_3$;

R$^2$ is (R)—CH$_3$CH(OH)— or (R)—CH$_3$CH(F)—;

R$^{a1}$ is halogen, —SCH$_3$, —S(O)$_2$CH$_3$ and —(C=O)H;

R$^{a3}$ is halogen, —SCH$_3$, —S(O)$_2$CH$_3$, —(C=O)H, —(S→O)CH$_3$ and —cyano; and M is a pharmaceutically acceptable cation or ester.

Also provided herein are preferred intermediates of the formula:

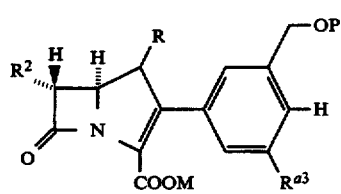

wherein R is H or CH$_3$, R$^2$ is (R)—CH$_3$CH(OP)— or (R)—CH$_3$CH(F)—, P is hydrogen or, independently, a readily removable protecting group for hydroxy, M is a readily removable carboxyl protecting group and R$^{a3}$ is I, —SMe, SO$_2$Me or Br.

DETAILED DESCRIPTION OF THE INVENTION

The manufacture of the bis-meta substituted phenyl compounds of formula I may be carried out by various schemes known to persons skilled in the art and including those schemes exemplified herein. Broadly, the compounds of the instant invention may be divided into five groups, each with preferred schemes of manufacture. These groups are defined by the atom of attachment of the bis-meta substituents on the 2-phenyl of carbapenem. The class names which follow are the halogen/halogen compounds, the halogen/carbon compounds, the halogen/sulfur compounds, the sulfur/sulfur compounds and the sulfur/carbon compounds.

The halogen/halogen compounds may be produced by the schemes demonstrated in Example 1. Halogen herein means fluorine, chlorine, bromine and iodine. Generally, the Grignard reaction of Example 1 may be used and any desired halogen substituted 2-phenyl substitutent may be obtained from the appropriate halogen substituted Grignard reagent. The desired Grignard reagent is made, as shown in Example 1, step (a), from an appropriately halogen substituted benzene. Many of the halogen substituted benzenes are commercially available. Example 3 details the production of 1,3,5-triiodobenzene. Specifically, the comparative 3' and 4'-halophenyl compounds of Tables I-VI were produced by the scheme of Examples 1 and 3 as were the inventive 3',5'-bis-substitutedphenyl compounds of Tables VII-IX.

The halogen/carbon compounds include the halogen/formyl and the halogen/nitrile and may be produced by the scheme of Example 2. As above with the halogen/halogen compounds, a Grignard reaction may be used and a halogen and hydroxymethyl substituted 2-phenyl substituent may be obtained from the appropriate halogen and hydroxymethyl substituted Grignard reagent. The desired Grignard reagent is made, as shown in Example 2, step (d), from an appropriately halogen and protected hydroxymethyl substituted benzene. Halogen and hydroxymethyl substituted benzenes are well within the skill of the art. Example 2, steps (a)–(b), exemplify the production of 3,5-dibromobenzylalcohol. Example 4, step (a), exemplifies the production of 3,5-diiodobenzaldehyde from which 3,5-diiodobenzylalcohol may be produced. The hydroxymethyl substituent serves as a precursor substituent to the formyl, —(C=O)H, and nitrile, —CN, groups. Example 2, step(g), exemplifies the oxidation of the hydroxymethyl precursor to formyl. The cyano substituent might be obtained from the formyl by exposing the formyl to hydroxylamine in an appropriate solvent at room temperature to produce the oxime, —CH=NOH, followed by dehydrating with triflic anhydride and triethylamine in a solvent at the appropriate temperature. Specifically, the bromo/formyl of Example 2 was produced and characterized in Tables VII-IX as was the iodo/formyl in Example 4 and Tables XIII-XV. Comparative compounds of the halogen/carbon type in Tables I-VI and Tables VII-IX were also produced by the scheme exemplified in Examples 2.

The halogen/sulfur compounds include the halogen/(SMe or (S→O)Me or S(O)$_2$Me) compounds and may be produced by schemes exemplified in Example 5, 6, 8 and 9. Again, the Grignard reaction may be used and a halogen and methylthio substituted 2-phenyl substituent may be obtained from the appropriate halogen and methylthio substituted Grignard reagent. The desired Grignard reagent is made, as shown in Example 5, step (b), from an appropriately halogen and methylthio substituted benzene. Halogen and methylthio substituted benzenes are well within the skill of the art. Example 5, step (a), exemplifies the production of 3,5-dibromothioanisole. The chlorine and fluorine equivalents may be easily produced by this scheme. Example 8, step (a), exemplifies the production of 3,5-diiodoanisole. Other methods to produce these substituted benzene starting materials will be apparent to persons skilled in the art. Using the 2-(3'-halo-5'-methylthiophenyl) carbapenem as a starting material, the schemes exemplified in Examples 6 and 9 may be used to produce the halo/((S→O)Me or S(O)$_2$Me) compounds. Accordingly, the halogen/sulfur compounds of Tables X-XV were produced by these methods.

The sulfur/sulfur compounds include the (SMe or S(O)$_2$Me)/(SMe or (S→O)Me or S(O)$_2$Me) compounds and may be produced by the scheme exemplified in Examples 5 and 7. The Grignard reaction may be used and a bis-methylthio substituted 2-phenyl substituent may be obtained from the appropriate bis-methylthio substituted Grignard reagent. The desired Grignard reagent is made, as analogously shown in Example 5, step (b), from an appropriately bis-methylthio substituted benzene. Bis-methylthio substituted benzenes are well within the skill of the art. Example 5, step (a), exemplifies the production of 3,5-bis-methylthiobromobenzene. Using 2-(3',5'-bis-methylthiophenyl) carbapenem as a starting material, Example 7 exemplifies a scheme by which the methylthio substituents may be oxidized to (S→O)Me or S(O)$_2$Me. Accordingly, the sulfur/sulfur compounds of Tables XIX-XXI were produced.

The sulfur/carbon compounds include the (SMe or (S→O)Me or S(O)$_2$Me)/(formyl or nitrile) compounds and may be produced by a scheme exemplified in Examples 5 and 2. Broadly, the 3,5-dibromothioanisole of Example 5, step (a), is substituted for the 1,3,5-tribromobenzene of Example 2, step (a). The resultant formyl substituent on benzene is subsequently replaced with protected hydroxymethyl per Example 2, steps (b)–(c) to produce a protected hydroxymethyl and methylthio substituted benzene. The Grignard reaction may be used and a protected hydroxymethyl and methylthio substituted 2-phenyl substituent may be obtained from the protected hydroxymethyl and methylthio substituted Grignard reagent. The desired Grignard reagent is made, as analogously shown in Example 2, step (d), from the protected hydroxymethyl and methylthio substituted benzene above. The protected hydroxymethyl substituent may be converted to formyl as in Example 2, step (g). The formyl might be converted to cyano as described above. The thiomethyl may be oxidized to (S→O)Me or S(O)$_2$Me as in Example 6. Accordingly, the compounds of Tables XVI-XVIII were produced and characterized.

In the preparation methods described above, the carboxyl group at the 3-position and, optionally, the hydroxyl group at the 8-position of the carbapenem remain blocked by protecting groups until the penultimate product is prepared. Suitable hydroxyl protecting groups, P, are silyl groups such as trialkylsilyl, aryl(alkyl)alkoxysilyl, alkoxydiarylsilyl and diarylalkylsilyl and carbonate groups such as alkyloxy and substituted alkyloxycarbonyl, benzyloxycarbonyl, substituted benzyloxycarbonyl, allyloxycarbonyl and substituted allyloxycarbonyl. The preferred protecting groups, in addition to or including those shown in the schemes, are t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups M, in addition to or including those shown in the schemes are described herein below. Deblocking may be carried out in a conventional manner. A suitable scheme is exemplified in Example 1, step (c).

It has been found in certain carbapenems that with certain 2-side-chain selections, the ultimate balance of properties in the overall molecule may be enhanced by selection of a 6-(R)(1-fluoroethyl) moiety instead of a 6-(R)(1-hydroxyethyl). Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 1985, 23, 1915; BE 900 718 A (Sandoz) and Japanese Patent Pub. No. 6-0163-882-A (Sanruku Ocean).

In preferred compounds of Formula I $R^1$ is hydrogen and $R^2$ is 6-(R)-(1-hydroxyethyl). While R=H is usually preferred, there are instances in which R=CH$_3$ might provide improved chemical stability, water solubility, or pharmacokinetic behavior. The substituent R=CH$_3$ may be of either configuration, i.e., the $\alpha$ or $\beta$-stereoisomer.

Listed in Table A are specific compounds of the instant invention:

TABLE A

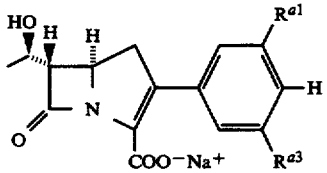

wherein $R^{a1}$ and $R^{a3}$ are simultaneously selected from the pairs of the group consisting of:

| $R^{a1}$ | Ra3 |
|---|---|
| F | F |
| Cl | Cl |
| Br | Br |
| Br | Cl |
| I | I |
| I | Br |
| I | Cl |
| Br | HC=O |
| I | HC=O |
| Br | SMe |
| Br | (S→O)Me |
| Br | S(O)$_2$Me |
| I | SMe |
| I | (S→O)Me |
| I | S(O)$_2$Me |
| SMe | SMe |
| SMe | (S→O)Me |
| (S→O)Me | S(O)$_2$Me |
| S(O)$_2$Me | S(O)$_2$Me |
| SMe | HC=O |
| (S→O)Me | HC=O |
| S(O)$_2$Me | HC=O |
| I | CN |
| HC=O | CN |
| (S→O)Me | CN and |

| $R^{a1}$ | Ra3 |
|---|---|
| S(O)$_2$Me | CN. |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Broadly, such ester protecting groups include alkyl, substituted alkyl, benzyl, substituted benezyl, aryl, substituted aryl, allyl, substituted allyl and triorganosilyl. Examples of specific such ester protecting groups include benzhydryl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, o-nitrobenzyl, 4-pyridylmethyl and t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

EXAMPLE 1

Step (a)

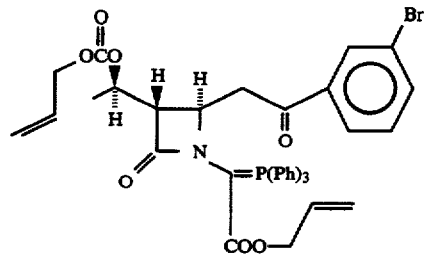

Preparation of
(3S,4R)-1-[[(allyloxy)carbonyl)](triphenylphosphoranylidene)methyl]-3-[(1R)-1-[allyloxycarbonyloxy)ethyl]-4-[[[(3-bromo)phenyl]carbonyl]methyl]azetidin-2-one Magnesium (264 mG,11 mM) was added to a solution of 1,3-dibromobenzene (2.36 G,10 mM) in 20 mL of anhydrous tetrahydrofuran. ~8 μL of 1,2-dibromoethane was added. After 2 hr. stirring at room temperature under nitrogen, most of the metal was digested and the resulting solution was used as 0.5 molar solution of 3-bromophenylmagnesiumbromide.

This Grignard solution (8 mL) was added dropwise to a solution of 1.4 G (2 mM) of (3S,4R)-1-[[(allyloxy)-carbonyl](triphenylphosphoranylidene) methyl]-3-[(1R)-1-[[(allyloxy)carbonyloxy]ethyl]-4-[(1R)-2'-[(pyridylthio)carbonyl]methyl]azetidin-2-one in 5 mL of tetrahydrofuran at 0° C. under nitrogen. After 15 minutes, 10 mL of saturated ammonium chloride solution was added, diluted with 25 mL of ethyl acetate and washed with 3×10 mL of saturated sodium chloride solution. After drying over anhydrous magnesium sulfate, solvent was removed from the organic phase to give a crude oil (yellow), which was chromatographed on silica gel using 2:3 mixture of ethyl acetate:hexane to give 720 mG of the desired ylide ketone as cream colored foam.

Step (b)

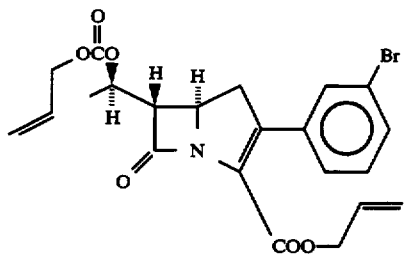

Preparation of allyl (5R,6S)-2-[3-bromophenyl]-6-[(1R)-allyloxycarbonyloxyethyl]-carbapen-2-em-3- carboxylate A solution of the ylid ketone (650 mG), from step (a) above, and two tiny crystals of hydroquinone in 4 mL of p-xylene was heated 3 hours at 130° under nitrogen. After cooling the reaction mixture, it was applied on a silica gel column packed with hexane. The column was eluted first with hexane and then with 1:3 mixture of ethyl acetate:hexane to give 300 mG of the desired carbapenem as colorless oil.

Step (c)

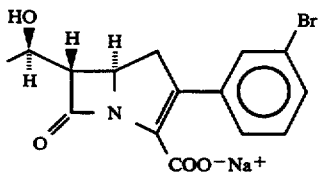

Preparation of sodium (5R,6S)-2-[3-bromophenyl]-6[(1R)-1-hydroxyethyl]-carbapen-2-em-3-carboxylate To a stirred solution of bis-allyl carbapenem of step (b), (225 mG,0.4727 mM) in 5 mL of 1:1 mixture of CH₂Cl₂:ether in a centrifuge tube under N₂ at 0° were added 2-ethylhexanoic acid (75 μL,0.472 mM), triphenylphosphine (33 mG, 0.135 mM), tetrakis-triphenylphosphine palladium (84 mG,0.075 mM), and sodium 2-ethylhexanoate (78 mG, 0.472 mM) sequentially. After 5 mins., a voluminous precipitate was observed. After an additional stirring of 2 hours, the reaction mixture was diluted with 10 mL of ether. After centrifugation, liquid was decanted. The solid was washed with 2 mL of ethylacetate. The resulting solid was dissolved in 2 mL of water and applied on 2×1000 μ reverse phase silica gel plates, and eluted with 1:4 mixture of acetonitrile and water. U.V. active area was scraped and stirred with 10 mL of 4:1 CH₃CN:water mixture. Solid was filtered and washed with 2×4 mL of the same solvent. The filtrate was washed with 4×25 mL of hexane, and concentrated to ~2 mL and freeze dried to give 104 mG of the desired sodium salt as a white fluffy mass.

EXAMPLE 2

Step (a)

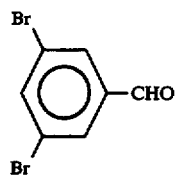

Preparation of 3,5-dibromobenzaldehyde 1.344 G (56 mM) of magnesium was added to a solution of 15-7 G(50 mM) of 1,3,5-tribromobenzene and the mixture was stirred at room temperature after 5 hours, most of the metal was digested. To the resulting brown Grignard solution was added 7.5 mL (0.1M) of N,N-dimethylformamide at 0° under nitrogen. The resulting mixture was stirred overnight at room temperature. Solvent was removed in vacuo at room temperature. The residue was taken up in 200 mL of ethyl acetate and washed with 6×50 mL of saturated sodium chloride solution, dried over anhydrous MgSO₄. Solvent was removed to give a crude solid, which was dissolved in minimum amount of CH₂Cl₂ and applied on silica gel. Elution with 1:9 mixture of ether:hexane containing methylene chloride gave 45% yield of the desired aldehyde as white solid.

Step (b)

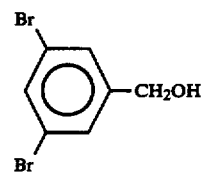

Preparation of 3,5-dibromobenzylalcohol 1.14 G(30 mM) of sodium borohydride was added slowly to a suspension of 3,5-dibromobenzaldehyde (7.92 G;30 mM), from step (a), in 50 mL of methanol at 0° under nitrogen. After stirring 30 mins., the reaction mixture was diluted with 150 mL of ethyl acetate and washed with 5×50 ml of saturated sodium chloride solution, dried over anhydrous magnesium sulfate. Solvent removal afforded a crude product, which was dissolved in minimum amount of CH₂Cl₂ and applied on silica gel. Elution with 1:2 mixture of EtOAc:hexane gave 7.2 G of the desired alcohol as white solid.

Step (c)

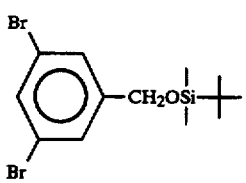

Triethylamine (3.22 mL; 23 mM), t-butyldimethyl silyl chloride (3.46 G; 23 mM), and 0.5 mL of N,N-dimethylformamide were added to a suspension of 3,5-dibromobenzyl alcohol (3.05 G; 11.46 mM), from step (c), in 50 mL of anhydrous methylene chloride. This reaction mixture was stirred overnight under nitrogen, and diluted with 75 mL of ethyl acetate. After washing with 3×25 mL of saturated sodium chloride solution, the organic phase was dried over anhydrous magnesium sulfate. Solvent removal gave the crude product as oil, which was distilled to give 2.7 G of the desired silyl ether as colorless oil, boiling at 120°/~1 mm.

step (d)

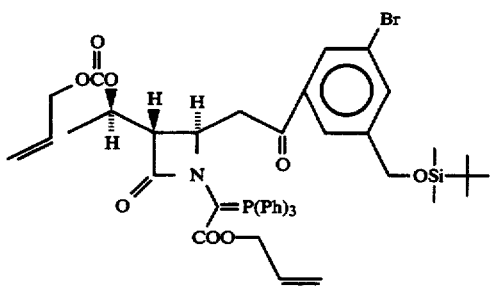

Preparation of (3S,4R)-1-[[(allyloxy)carbonyl)](triphenylphosphoranylidene) methyl]-3-[(1R)-1-allyloxycarbonyloxy)ethyl]-4-[[[(3-(t-butyldimethylsilyl)oxymethyl)-5-bromophenyl]carbonyl]methyl]azetidin-2-one This ylid ketone was prepared according to the procedure of step (a) in Example 1, using the silyl ether from step (c) of this example.

Step (e)

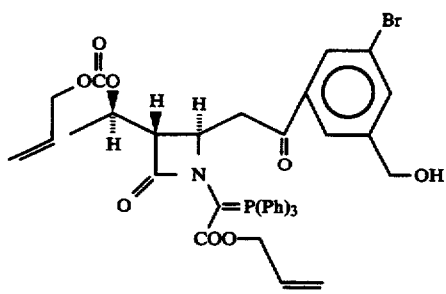

Preparation of (3S,4R)-1-[[(allyloxy)carbonyl](triphenylphosphoranylidene) methyl]-3-[(1R)-1-allyloxycarbonyloxy)ethyl]-4-[[[(3-hydroxymethyl)-5-bromophenyl]carbonyl]methyl]azetidin-2-one 18 mL of ice cold 2% sulfuric acid solution in methanol was added to 1.2 G (1.4 mm) of foamy silyl ether from step (d), and the resulting solution was stirred 1.5 hours at 0°. After diluting with 30 mL of ethyl acetate, the reaction mixture was washed with 3×15 mL of 10% sodium bicarbonate solution. The organic phase was dried over anhydrous magnesium sulfate. Solvent removal gave a crude yellow product, which was purified on silica gel using 2:1 ethyl acetate: hexane mixture as solvent to give 880 mG of the desired alcohol as white foam.

Step (f)

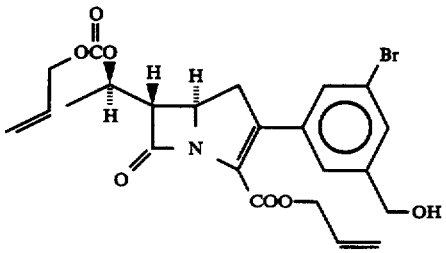

Preparation of allyl (5R,6S)-2-[(3-hydroxymethyl)(5-bromo)phenyl]-6-[(1R)-1-allyloxycarbonyloxyethyl]carbapen-2-em-3-carboxylate This carbapenem carbinol was obtained as oil following the procedure described in step (b) of Example 1, using the ylid ketone from step (e) of this example.

Step (g)

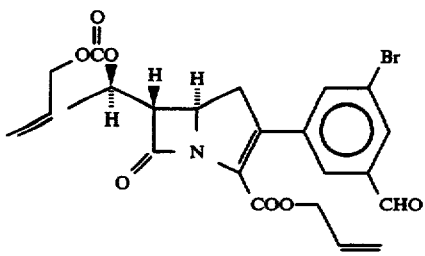

Preparation of allyl (5R,6S)-2-[(3-aldehydo)-(5-bromo)phenyl]-6-[(1R)-1-allyloxycarbonyloxyethyl]carbapen-2-em-3-carboxylate To a solution of 350 mG (0.716 mM) of the carbapenem alcohol, from step (f), in 8.5 ml of methylene chloride at room temperature under nitrogen were added 55 mG of powdered 3Å molecular sieves, and 126 mG (1.074 mM) of N-methyl morpholine N-oxide. After stirring 5 mins., 25 mG (0.0716 mM) of tetra-n-propylammonium perrhuthenate was added and stirred for additional 10 mins. This was then filtered through a bed of 25 G of silica gel and washed with 5×10 mL of ethyl acetate. Concentration of the filtrate at room temperature in vacuo gave 295 mG of the desired aldehyde as oil.

Step (h)

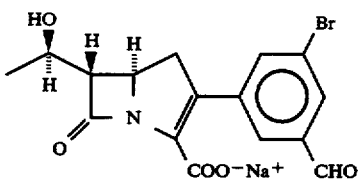

Preparation of sodium (5R,6S)-2-[(3-aldehydo)-(5-bromo)phenyl]-6-[(1R)-1-hydroxyethyl]carbapen-2-em-3-carboxylate This sodium salt was prepared according to the procedure given in step (c) of Example 1, using the carbapenem in step (g) of this example.

EXAMPLE 3

Step (a)

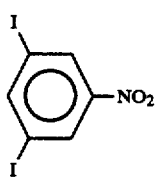

Preparation of 3,5-diiodonitrobenzene 13.8 G (0.2M) of solid sodium nitrite were slowly added to stirred concentrated sulfuric acid at 0° C. The resulting thick mixture was stirred at 0° C. for 10 mins. A suspension of 68.28 G (0.175M) of finely powdered 2,6-diiodo-4-nitroaniline in 175 mL of glacial acetic acid was added portionwise cautiously to the above mixture at 0° C. over a period of 25 minutes. This mixture was then stirred 30 mins, and then added to a vigorously stirred suspension of 4 G of cuprous oxide in 420 mL of absolute ethanol over a period of 25 minutes. Vigorous effervescence was observed during this addition. The resulting mixture was stirred 20 mins. at room temperature and then heated to reflux for 30 mins. After cooling, this reaction mixture was poured into large amount of ice. Solid separated was filtered, and washed with water. This solid was dissolved in minimum amount of chloroform, and dried over anhydrous magnesium sulfate. Solvent removal gave 62 G of 3,5-diiodo-nitrobenzene as light yellow solid.

Step (b)

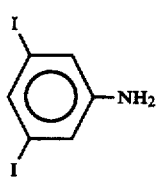

Preparation of 3,5-diiodoaniline

A mixture of 61.5 G (0.164M) of 3,5-diiodonitrobenzene, from step (a), and 111.1 G (0.4924M) of stannous chloride in 900 ml of absolute ethanol was heated to reflux 1.5 hours under nitrogen. Most of the solvent was removed. The residue was stirred with ethylacetate, 5 normal sodium hydroxide and ice. organic phase was separated and washed with saturated sodium chloride solution. After drying over anhydrous magnesium sulfate, solvent was removed to afford a crude oil, which was chromatographed on silica gel using 8:1:1 mixture of hexane:methylene chloride:ethyl acetate. The desired aniline was obtained as 35 G of light tan colored solid.

Step (c)

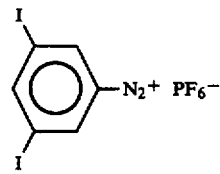

Preparation of 3,5-diiodophenyldiazonium hexafluorophosphate 3.8 G (55 mM) of sodium nitrite was slowly added to 37.5 mL of ice cold concentrate sulfuric acid. To this stirred slurry at 0° was added a suspension of 17.25 G (50 mM) of 3,5-diiodoaniline, from step (b), in 137.5 ml of glacial acetic acid slowly over a period of 10 mins. After stirring 30 mins. at 0°, a solution of 18.4 G (0.1M) of potassium hexafluorophosphate in 250 ml of water was added dropwise. A light tan colored solid separated. After 30 min. vigorous stirring, the solid was filtered and washed several times with 4:1 mixture of ether and methanol, and then a few times with ether. Solid was dried in vacuo to give 22.85 G of the desired diazonium salt as light tan colored solid.

Step (d)

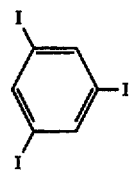

Preparation of 1,3,5-triiodo benzene

A solution of 7.5 G (50 mM) of sodium iodide in 40 mL of acetone was slowly added to a stirred suspension of the diazonium salt (12.5 G; 25 mM), from step (c), in 175 mL of acetone at 0°. The addition took about 25 mins. The reaction mixture was stirred for 2 hours at 0°. Solvent was removed in vacuo at room temperature, and the residue was stirred with water. The tan colored solid was filtered and washed several times with water, and dried in vacuo to give 9.05 G of 1,3,5-triiodobenzene as tan colored solid.

step (e)

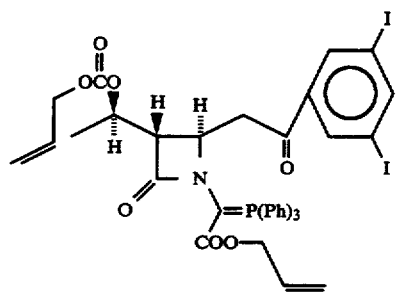

Preparation of
(3S,4R)-1-[[(allyloxy)carbonyl)](triphenylphosphoranylidene)methyl]-3-[(1R)-1-(allyloxycarbonyloxy)ethyl]-4-[[[(3,5-diiodo)phenyl]carbonyl]methyl]azetidin-2-one n-Butyllithium (2.5M; 2 ml; 5 mM) was added dropwise to a stirred suspension of 1,3,5-triiodobenzene (1.368 G; 3 mM) in 12 mL of anhydrous ether over 2 mins. The reaction mixture was stirred 15 mins. at −78° C. Then a freshly prepared solution of magnesium bromide, from 144 mG (6 mM) of magnesium and 523 μL (6 mM) of 1,2-dibromo-ethane in 24 mL of anhydrous tetrahydrofuran, was added slowly over 5 mins. The resulting suspension was stirred 15 mins. at −78° C. and 30 mins at 0° C. The resulting turbid solution was used as 0.0833 molar solution of 3,5-diiodophenyl magnesium bromide.

This solution was treated with 704 mG (1 mM) of the thioester as described in step (a) of example 1 to give 430 mG of the desired ylid ketone as yellow foam.

step (f)

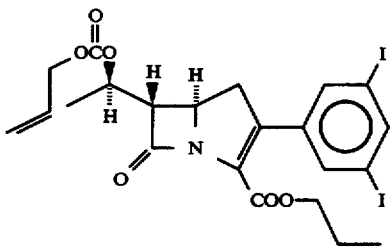

Preparation of allyl
(5R,6S)-2-[(3,5-diiodo)phenyl]-6-[1R-(allyloxy)carbonyloxyethyl]-carbapen-2-em-3-carboxylate This carbapenem was prepared from the ylid ketone of step (e) of this example, using the procedure of step (b) of Example 1.

step (g)

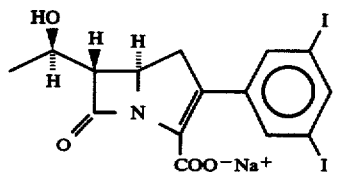

Preparation of sodium
(5R,6S)-2-[(3,5-diiodo)phenyl]-6-[1R-1-hydroxyethyl]-carbapen-2-em-3-carboxylate This sodium salt was prepared from the bis-allyl protected carbapenem of step (f) of this example, using the procedure of step (c) of Example 1.

EXAMPLE 4 step (a)

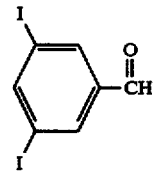

Preparation of 3, 5-Diiodobenzaldehyde

To a slurry of 1,3,5-triiodobenzene (7.5 G, 16.4 mM) in 72 mL of ether at −78° was added n-butyllithium 7.2 mL; 18 mM). After 15 minutes of stirring, 2.8 mL (36 mM) of N,N-dimethylformamide was added dropwise and the reaction mixture was stirred overnight. After diluting with 100 mL of ethyl acetate, the reaction mixture was washed with 3×50 mL of saturated sodium chloride solution, and dried over anhydrous magnesium sulfate. Solvent removal gave a crude product, which was chromatographed on silica gel (application in minimum amount of $CH_2Cl_2$; and elution with 1:9 EtOAc:-hexane) to yield 1.3 G of the desired aldehyde as cream colored solid.

steps (b)-(h)

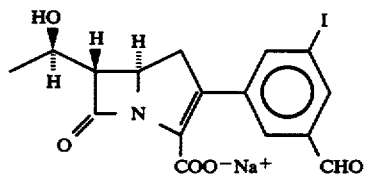

Preparation of sodium
(5R,6S)-2-[(3-aldehydo-5-iodo)phenyl]-6-[1R-1-hydroxyethyl]-carbapen-2-em-3-carboxylate This sodium salt was prepared from the 3,5-diiodo benzaldehyde of step (a) of this example, using the procedure of steps (b) and (c) of Example 2, the procedure of Example 3, step (e), and finally the procedure of Example 2, steps (e)-(g).

EXAMPLE 5 step (a)

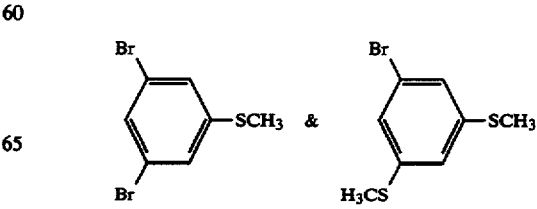

Preparation of 3, 5-Dibromothioanisole and 3, 5-(Bis-methylthio)Bromobenzene A mixture of 5 G (0.208M) of magnesium, and 63 G (0.2M) of 1, 3, 5-tribromobenzene in 400 mL of tetrahydrofuran was stirred 5 hrs. at room temperature under nitrogen, when most of the metal was digested.

The resulting solution was cooled to ~10° C., and dimethyldisulfide (37.6; 0.4M) was added dropwise, and the resulting mixture was stirred overnight at room temperature. After diluting with 500 ml of ethyl acetate and washed with 5×200 mL of saturated sodium chloride solution, the organic phase was dried over anhydrous magnesium sulfate, and the solvent was removed to give crude brown oil.

This was purified on silica gel using hexane as solvent to give 50% of 3,5-dibromothioanisole boiling at ~110° at 1 mm, and 8% of 3,5-(bis-methylthio)bromobenzene boiling at 130°-5° at 1 mm, which solidified slowly on standing.

steps (b)–(c)

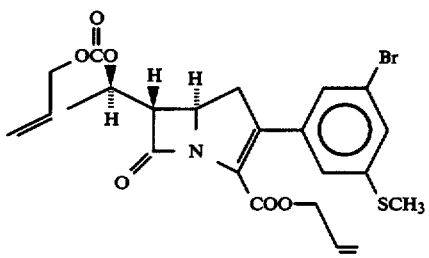

Preparation of allyl (5R,6S)-2-[3-methylthio-5-bromo)phenyl]-6-[1R-1-allyloxycarbonyloxyethyl]carbapen-2-em-3-carboxylate This carbapenem was prepared from the 3,5-dibromothioanisole of step (a) of this example, using the procedure of steps (a)–(b) of Example 1.

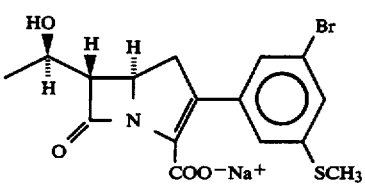

Preparation of sodium (5R,6S)-2-[3-methylthio-5-bromo)phenyl]-6-[1R-1-hydroxyethyl]-carbapen-2-em-3-carboxylate This sodium salt was prepared from the carbapnem allylester of step (c) of this example, using the procedure of step (c) of Example 1.

EXAMPLE 6 step (a)

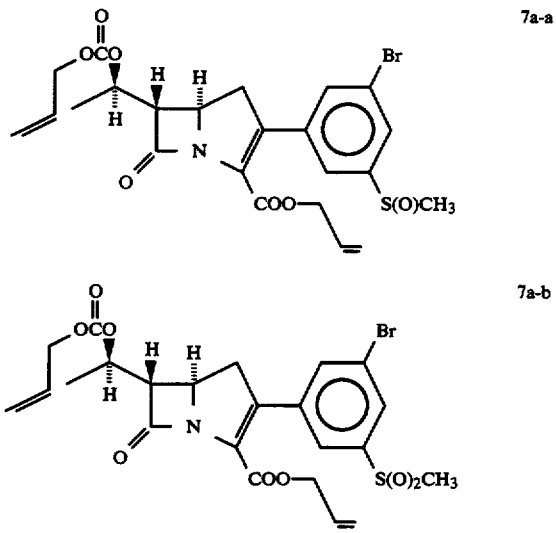

Preparation of allyl (5R,6S)-2-[3-methylsulfinyl-5-bromophenyl]-6-[1R-1-allyloxycarbonyloxyethyl]carbapen-2-em-3-carboxylate (7a–a) and allyl (5R,6S)-2-[3-methylsulfonyl-5-bromophenyl]-6-[1R-1-allyloxycarbonyloxyethyl]-carbapen-2-em-3-carboxylate (7a–b)

To a solution of the allyl ester of the carbapenem sulfide (232 mG,0.44 mM) from step (c) of Example 5 in 5.5 mL of methylene chloride under nitrogen at 0° C. were added 2.8 mL of 0.5M sodium bicarbonate solution and 114 mG (0.66 mM) of m-chloroperbenzoic acid. The reaction mixture was stirred vigorously for 1 hr. Subsequently, 10 mL of 5% sodium thiosulfate was added and stirred an additional 1 hr. It was then diluted with 15 mL of ethyl acetate and washed with 3×10 mL of saturated sodium chloride solution. The organic phase was dried over anhyd. magnesium sulfate. Solvent removal gave a crude oil, which was purified on silica gel using 1:1 ethyl acetate:hexane mixture as eluant. 39 mG of the sulfone (7a–b) and 130 mG of the sulfoxide (7a–a) were obtained as oils.

step (b)

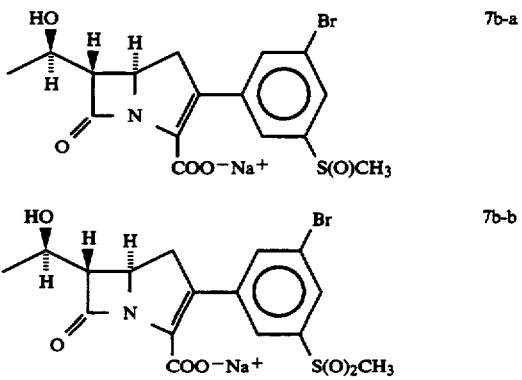

Preparation of sodium
(5R,6S)-2-[3-methylsulfinyl-5-bromophenyl]-6-[1R-1-hydroxyethyl]carbapen-2-em-3-carboxylate (7b–a) and sodium
(5R,6S)-2-[3-methylsulfonyl-5-bromophenyl]-6-[1R-1-hydroxyethyl]carbapen-2-em-3-carboxylate (7b–b)

These sodium salts were prepared from the carbapenem allyl esters from step (a) of this example following the procedure described in step (c) of Example 1.

EXAMPLE 7 step (a)

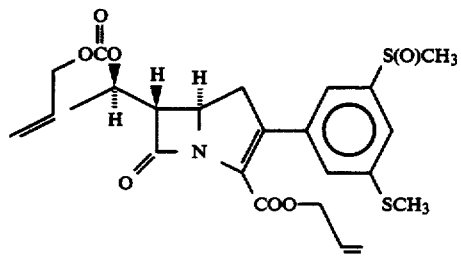
8a-a

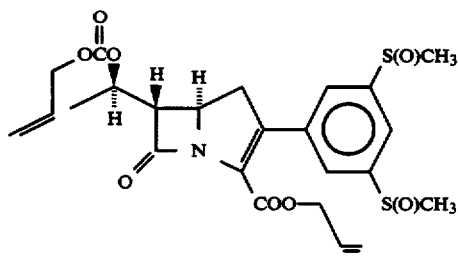
8a-b

Preparation of allyl
(5R,6S)-2-[3-methylsulfinyl-5-methylthiophenyl]-6-[1R-1-allyloxycarbonyloxyethyl]carbapen-2-em-3-carboxylate (8a–a) and allyl
(5R,6S)-2-[3,5-(bis-methylsulfinyl)phenyl]-6-[1R-1-allyloxycarbonyloxyethyl]-carbapen-2-em-3-carboxylate (8a–b)

To a solution of the carbapenem disulfide (195 mG, 0.4 mM) in 5 mL of methylene chloride were added 2.5 mL 0.5M sodium bicarbonate and 102 mG (0.59 mM) of m-chloroperbenzoic acid at 0° C. under nitrogen. The mixture was stirred for 1 hr. 10 mL of 5% sodium thiosulfate was added and the mixture was stirred for 1 hr. more. After diluting with 10 mL of ethyl acetate, the reaction mixture was washed with 3×5 mL of saturated sodium chloride solution. The organic phase was dried over anhydrous magnesium sulfate. Solvent removal gave a crude product which was purified on silica gel using 3:1 ethyl acetate:hexane as solvent to give 60 mG of the monosulfoxide (8a–a). Further elution with 15% methanol in ethyl acetate gave 75 mG of the bis-sulfoxide (8a–b).

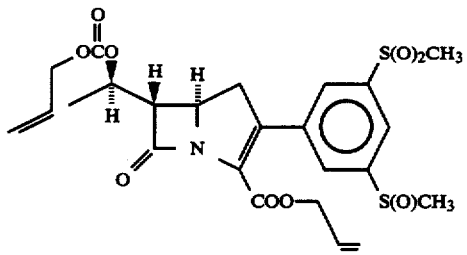
8a-c

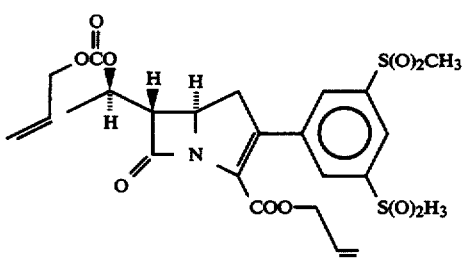
8a-d

By using a 3 equivalents of m-chloroperbenzoic acid instead of only 1.5 equivalents in the above procedure mono-sulfone sulfoxide carbapenem 8a–c and bis-sulfone carbapenem 8a–d were obtained.

Step (b)

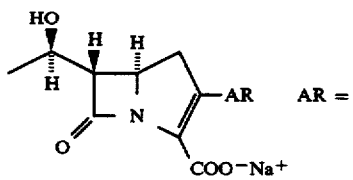

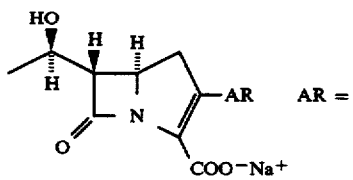
8b-a    8b-b

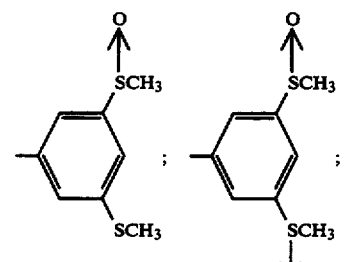

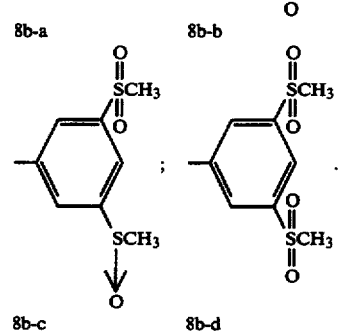
8b-c    8b-d

Preparation of sodium
(5R,6S)-2-[(3-methylsulfinyl)(5-methylthio)phenyl]-6-[(1R)-hydroxyethyl]carbapen-2-em-3-carboxylate (8b–a) and its three analogs (8b–b), (8b–c) and (8b–d)

These sodium salts were prepared from the carresponding carbapenem allyl esters from Step (a) of this example by using the procedure described in Step (c) of Example 1.

EXAMPLE 8 step (a)

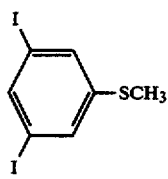

Preparation of 3,5-diiodothioanisole

Solid diazonium salt from Ex. 4, step (c) (9.1 G; 18.12 mM) was added to a stirred solution of potassium ethyl xanthate (5.81 G; 36.25 mM) in 90 mL of acetone at 0°. After stirring the reaction mixture 1 hr. solvent was removed in vacuo at room temperature and the residue was stirred with 50 ml of methylene chloride and ice water. The aqueous layer was washed with 2×50 ml of methylene chloride. The combined organic layers were washed with saturated sodium chloride, dried over anhydrous. MgSO₄, and solvent was removed to give ~5.1 G of the crude product.

To a stirred turbid solution of this xanthate derivative in ~50 mL of dry THF at 0° were added 3.3 ml of ethylenediamine and 2.8 mL of methyl iodide in that order. The reaction mixture was stirred 2.5 hrs. After diluting with 100 mL of ether, this was washed with ice-cold 2 normal HCl. The organic phase was washed with saturated sodium chloride and dried over anhydrous MgSO₄. Solvent removal gave crude product, which was chromatographed on silica gel (1:50 EtOAc:hexane) and distilled at oilbath temp. of 210° at ~0.01 mm to give 2.45 G of the desired product as oil, which slowly solidified.

Step (b)

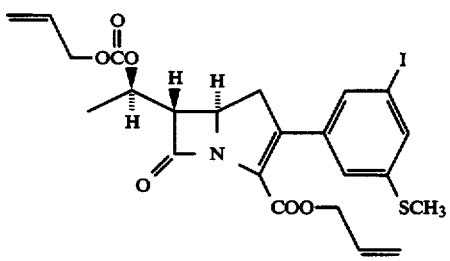

Preparation of allyl (5R,6S)-2-[(3-methylthio)-5-iodophenyl]-6-[(1R)-1-allyloxycarbonyloxyethyl]carbapen-2-em-3-carboxylate This carbapenem was prepared from diiodo-thioanisole emplying the methodology described in Steps (e) and (f) of Example 3.

Step (c)

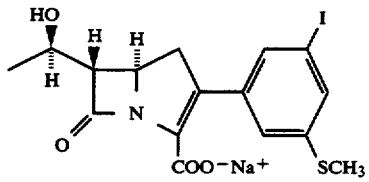

Preparation of sodium (5R, 6S)-2-[(3-methylthio)-5-iodophenyl]-6-[(1R)-1-hydroxyethyl]carbapen-2-em-3-carboxylate This carbapenem sodium salt was prepared from the allyl ester from step (b) of this example by using the procedure described in step (c) of Example 1.

EXAMPLE 9

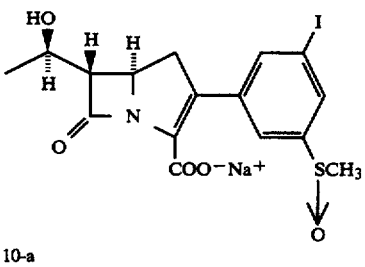

10-a

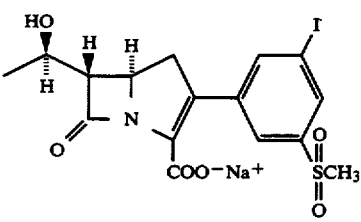

10-b

Preparation of sodium (5R, 6S)-2-[(3-methylsulfinyl)-5-iodophenyl]-6-[(1R)-1-hydroxyethyl]carbapen-2-em-3-carboxylate (10-a) and its 3-methylsulfonyl analog (10-b)

These carbapenem sodium salts were prepared from the sulfide of Step (b) of Example 8 by using the procedures described in Step (a) of Example 6 and Step (c) of example 1.

TABLE I
CHARACTERIZING DATA

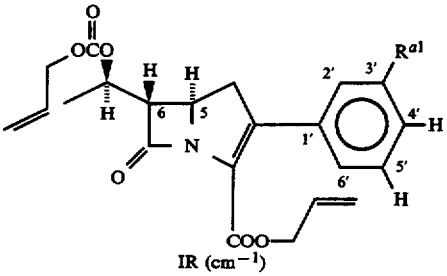

IR (cm⁻¹)

| | (C=O) | | |
|---|---|---|---|
| $R^{a1}$ | B-LACTAM | CARBONATE | ESTER |
| F | 1780 | 1740 | 1720 |

TABLE I-continued
CHARACTERIZING DATA

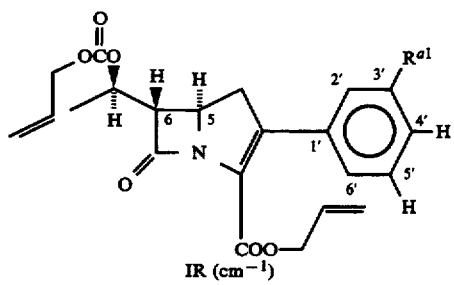

IR (cm$^{-1}$)

| | (C=O) | | |
|---|---|---|---|
| $R^{a1}$ | B-LACTAM | CARBONATE | ESTER |
| Cl | 1785 | 1745 | 1720 |
| Br | 1780 | 1740 | 1720 |
| I | 1780 | 1740 | 1720 |
| —CH$_2$OH | 1780 | 1745 | 1720 |
| | [ ⸺ 3500(OH)] | | |
| —CHO | 1780 | 1745 | 1720 |
| (1695; CHO) | | | |

TABLE II

| | NMR | | |
|---|---|---|---|
| $R^{a1}$ | H$_5$ | H$_6$ | H$_{2'}$–H$_{6'}$ |
| F | 4.22–4.37 ddd; J=3, 9 &9Hz | 3.38–3.47 dd; J=3&8.5Hz | 7–7.38 AROMATIC H's |
| Cl | 4.22–4.37 ddd; J=3, 8.5 &9Hz | 3.38–3.47 dd; J=3&8Hz | 7.2–7.36 AROMATIC H's |
| Br | 4.22–4.36 ddd; J=3, 9 &9.5Hz | 3.38–3.46 dd; J=3&8.5Hz | 7.16–7.5 AROMATIC H's |
| I | 4.22–4.35 ddd; J=3, 9 &8Hz | 3.38–3.46 dd; J=3&8Hz | 7.03–7.7 AROMATIC H's |
| CH$_2$OH | 4.23–4.35 ddd; J=3, 9 &9Hz | 3.38–3.46 dd; J=3&8.5Hz | 7.23–7.40 AROMATIC H's |
| CHO | 4.21–4.33 ddd; J=3, 8 &9Hz | 3.35–3.47 dd; J=3&8.5Hz | 7.4–7.4 AROMATIC H's 9.93(CHO) |

TABLE III

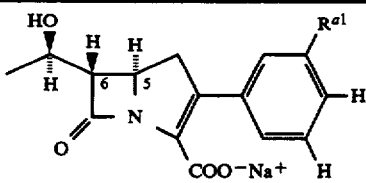

| | UV (nm) | | |
|---|---|---|---|
| $R^{a1}$ | $\lambda_{max}$ | $\epsilon_{ext}$ | NMR (D$_2$O) |
| F | 300 | 7356 | 3.38–3.46 H6; dd; J=3&6Hz 6.94–7.33 AROMATIC H'S |
| Cl | 300 | 6815 | 3.42–3.50 H6; dd; J=3&6Hz 7.17–7.35 AROMATIC H'S |
| Br | 300 | 7738 | 3.43–3.50 H6; dd; J=3&6Hz 7.18–7.52 AROMATIC H's |
| I | 302 | 7814 | 3.38–3.46 H6; dd; J=3&6Hz 6.97–7.66 AROMATIC H's |
| CH$_2$OH | 300 | 9230 | 3.45–3.53 |

TABLE III-continued

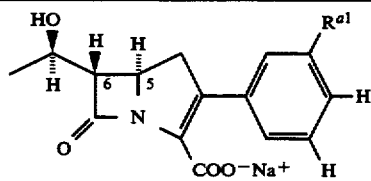

| | UV (nm) | | |
|---|---|---|---|
| $R^{a1}$ | $\lambda_{max}$ | $\epsilon_{ext}$ | NMR (D$_2$O) |
| CHO | 300 | 7752 | H6; dd; J=3&6Hz 7.24–7.38 AROMATIC H's 3.44–3.51 H6; dd; J=3&6Hz 7.44–7.84 AROMATIC H's |

TABLE IV

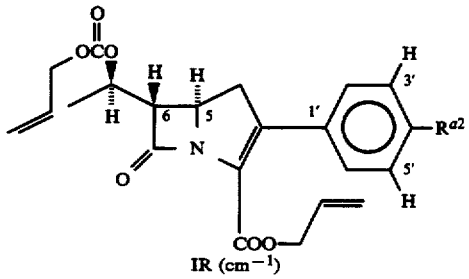

IR (cm$^{-1}$)

| | (C=O) | | |
|---|---|---|---|
| $R^{a2}$ | B-LACTAM | CARBONATE | ESTER |
| F | 1780 | 1745 | 1720 |
| Cl | 1785 | 1745 | 1725 |
| Br | 1785 | 1745 | 1720 |
| I | 1780 | 1745 | 1720 |
| CH$_2$OH | 1780 | 1745 | 1725 |
| CHO | 1780 | 1740 | 1720 |

TABLE V

| $R^{a1}$ | H$_5$ | H$_6$ | H$_{2'}$–H$_{6'}$ |
|---|---|---|---|
| F | 4.21–4.33 ddd; J=3, 9&9.5Hz | 3.37–3.45 dd: J=3&8.5 Hz | 6.98–7.41 (AROMATIC H's) |
| Br | 4.22–4.34 ddd; J=3, 9.5&9Hz | 3.38–3.46 dd: J=3&8 Hz | 7.2–7.52 (AROMATIC H's) |
| CH$_2$OH | 4.23–4.35 ddd; J=3, 9&9.5Hz | 3.38–3.45 dd; J=3&9.5 Hz | 7.36 (AROMATIC H's) |
| CHO | 4.28–4.40 ddd; J=3, 8.5 &9.5Hz | 3.42–3.50 dd; J=3&8.5 Hz | 7.46–7.9 (AROMATIC H's) (10.03; CHO) |

TABLE VI

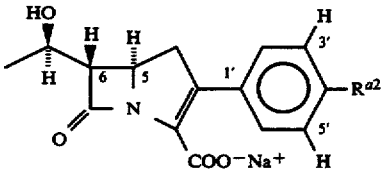

| | UV (nm) | | |
|---|---|---|---|
| $R^{a2}$ | $\lambda_{max}$ | $\epsilon_{ext}$ | NMR (D$_2$O) |
| F | ~298 | 6823 | 3.4–3.48(H6; dd; J=3&6Hz) 7–7.36(AROMATIC PROTONS) |

TABLE VI-continued

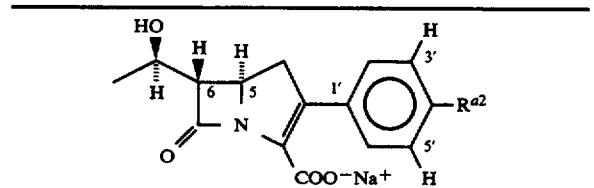

| $R^{a2}$ | UV (nm) $\lambda_{max}$ | $\epsilon_{ext}$ | NMR (D$_2$O) |
|---|---|---|---|
| Cl | ~303 | 6195 | 3.38–3.46(H6; dd; J=3&6Hz) 7.2–7.35(AROMATIC PROTONS) |
| Br | ~304 | 8378 | 3.42–3.50(H6; dd; J=3&6Hz) 7.18–7.5(AROMATIC PROTONS) |
| I | ~307 | 9767 | 3.44–3.52(H6; dd; J+3&6Hz) 7.06–7.73(AROMATIC PROTONS) |
| CHO | ~336 | 10724 | 3.4–3.48(H6; dd; J=3&6Hz) 7.38–7.82(AROMATIC PROTONS) |

TABLE VII

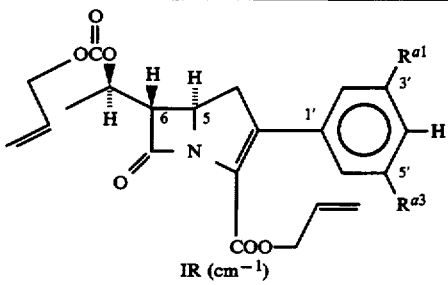

| | | IR (cm$^{-1}$) C=O | | |
|---|---|---|---|---|
| $R^{a1}$ | $R^{a2}$ | B-LACTAM | CARBONATE | ESTER |
| F | F | 1785 | 1745 | 1725 |
| Cl | Cl | 1790 | 1745 | 1725 |
| Br | Br | 1785 | 1740 | 1720 |
| I | I | 1785 | 1745 | 1725 |
| Br | CH$_2$OH | 1780 | 1745 | 1720 |
| Br | CHO | 1780 | 1745 | 1720 |

(CHO; 1705)

TABLE VIII

| | | NMR | | |
|---|---|---|---|---|
| $R^{a1}$ | $R^{a3}$ | H$_5$ | H$_6$ | H$_{2'}$–H$_{6'}$ |
| F | F | 4.24–4.36 ddd; J=3, 8&9.5Hz | 3.4–3.48 dd; J=3&8 Hz | 6.72–6.91 AROMATIC H's |
| Cl | Cl | 4.22–4.36 ddd; J=3, 9&9Hz | 3.4–3.48 dd; J=3&8.5 Hz | 7.2(d; H$_{2'}$&H$_{6'}$; J=2Hz) 7.31(t; H$_{4'}$; J=2Hz) |
| Br | Br | 4.24–4.38 ddd; J=3, 8 &8.5Hz | 3.4–3.48 dd; J=3&8.5 Hz | 7.42(d; H$_{2'}$&H$_{6'}$; J=2Hz) 7.64(t; H$_{4'}$; J=2Hz) |
| I | I | 4.22–3.36 ddd; J=3, 9 9.5 Hz | 3.38–3.46 dd; J=3&8Hz | 7.62(d; H$_{2'}$&H$_{6'}$; J=1.5Hz) 8.02(t; H$_{4'}$; J=1.5Hz) |
| Br | CH$_2$OH | 4.22–4.36 ddd; J=3, 8 &8.5Hz | 3.38–3.46 dd; J=3&8Hz | 7.28, 7.4, 7.49 AROMATIC H's 1.9(t; OH; J=~6Hz) |
| Br | CHO | 4.2–4.33 ddd; J=3, 8.5&9Hz | 3.35–3.43 dd; J=3&8Hz | 7.69, 7.73&7.89 AROMATIC H's 9.77, CHO |

TABLE IX

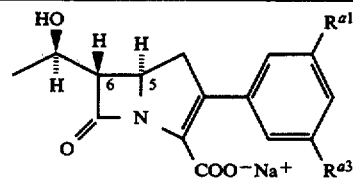

| $R^{a1}$ | $R^{a3}$ | UV (nm) $\lambda_{max}$ | $\epsilon_{ext}$ | NMR (D$_2$O) |
|---|---|---|---|---|
| F | F | 298 | 5528 | 3.44–3.50 (H6; dd; J=3&6Hz) 6.87&6.92 AROMATIC H's |
| Cl | Cl | 303 | 5533 | 3.44–3.50 (H6; dd; J=3&6Hz) 7.24&7.33 AROMATIC H's |
| Br | Br | 303 | 5255 | 3.42–3.48 (H6; dd; J=3&6Hz) 7.43&7.63 AROMATIC H's |
| I | I | 305 | 6892 | 3.8–3.86 (H6; dd; J=3&6Hz) 8.04&8.42 AROMATIC H's |
| Br | CH$_2$OH | 303 | 9777 | 3.44–3.52 (H6; dd; J=3&6Hz) 7.24&7.42 AROMATIC H's 4.27(CH$_2$O) |
| Br | CHO | 302 | 7718 | 3.46–3.54 (H6; dd; J=3&6Hz) 7.76&7.82 AROMATIC H's 9.78(CHO) |

TABLE X

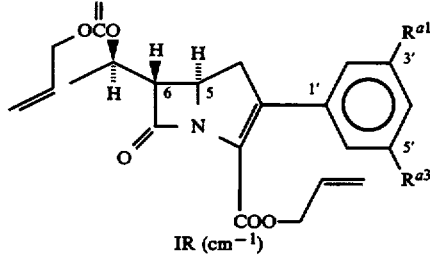

| | | IR (cm$^{-1}$) (C=O) | | |
|---|---|---|---|---|
| $R^{a1}$ | $R^{a3}$ | B-LACTAM | CARBONATE | ESTER |
| Br | SCH$_3$ | 1780 | 1740 | 1715 |
| Br | (S→O)CH$_3$ | 1785 | 1745 | 1725 |
| Br | S(O)$_2$CH$_3$ | 1785 | 1745 | 1725 |

TABLE XI

| | | NMR | | |
|---|---|---|---|---|
| $R^{a1}$ | $R^{a3}$ | H$_5$ | H$_6$ | H$_{2'}$–H$_{6'}$ |
| Br | SCH$_3$ | 4.26–4.38 ddd; J=3; 8.5&8.5Hz | 3.42–3.5 dd; J=3&8.5 Hz | 7.18; 7.26; 7.34 AROMATIC PROTONS 2.51(S; SCH$_3$) |
| Br | (S→O)CH$_3$ | 4.28–4.42 ddd; J=3; 9 &9Hz | 3.44–3.52 dd; J=3&8.5 Hz | 7.61; 7.64; 7.76 AROMATIC PROTONS 2.79(S; (S→O)CH$_3$) |
| Br | S(O)$_2$CH$_3$ | 4.28–4.42 | 3.44–3.52 | 7.78; 7.88; 8.04 |

TABLE XI-continued

| $R^{a1}$ | $R^{a3}$ | NMR H5 | H6 | H2'–H6' |
|---|---|---|---|---|
| | | ddd; J=3, 9 & 9.5Hz | dd; J=3&8Hz | AROMATIC PROTONS 3.08(S; S(O)$_2$CH$_3$) |

TABLE XIV-continued

| $R^{a1}$ | $R^{a3}$ | NMR H5 | H6 | H2'–H6' |
|---|---|---|---|---|
| | | 8.5&9Hz | 8.5Hz | |
| I | CHO | 4.28–4.40 ddd; J=3, 8&9Hz | 3.43–3.50 dd; J=3&8Hz | 7.84, 7.96&8.18 AROMATIC H's 9.92(CHO; s) |

TABLE XII

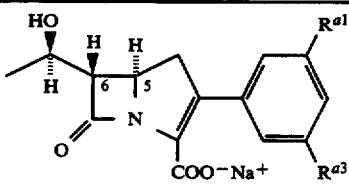

| $R^{a1}$ | $R^{a3}$ | UV (nm) $\lambda_{max}$ | $\epsilon_{ext}$ | NMR (D$_2$O) |
|---|---|---|---|---|
| Br | SCH$_3$ | ~304 | 8064 | 3.38–3.46(H6; dd; J=3&6 2.38(SCH3); 7.12; 7.2; 7.3(AROMATIC PROTONS) |
| Br | (S→O)CH$_3$ | ~306 | 8720 | 3.45–3.52(H6; dd; J=3&6Hz) 2.82((S→O)CH$_3$)7.54;7.66; 7.74(AROMATIC PROTONS) |
| Br | S(O)$_2$CH$_3$ | ~308 | 8678 | 3.48–3.55(H6; dd; J=3&6Hz) 3.22(S(O)$_2$CH$_3$)7.83; 8.0 (AROMATIC PROTONS) |

TABLE XIII

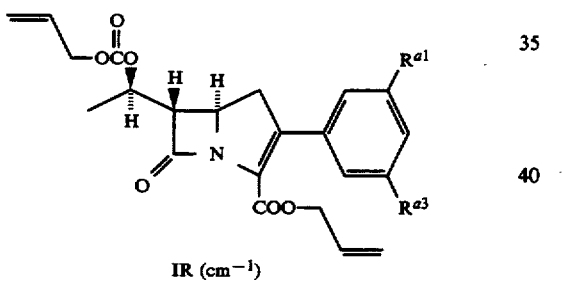

| | | IR (cm$^{-1}$) (C=O) | | |
|---|---|---|---|---|
| $R^{a1}$ | $R^{a3}$ | B-LACTAM | CARBONATE | ESTER |
| I | SCH$_3$ | 1780 | 1740 | 1720 |
| I | (S→O)CH$_3$ | 1780 | 1740 | 1725 |
| I | S(O)$_2$CH$_3$ | 1780 | 1740 | 1725 |
| I | CH$_2$OH | 1775 | 1745 | 1725 |
| I | CHO | 1780 | 1745 1705(CHO) | 1725 |

TABLE XIV

| $R^{a1}$ | $R^{a3}$ | NMR H5 | H6 | H2'–H6' |
|---|---|---|---|---|
| I | SCH$_3$ | 4.23–4.35 ddd; J=3, 8.5&9 | 3.4–3.48 dd; J=3& 8.5Hz | 7.2, 7.43&7.54 AROMATIC H's 2.41.(SCH$_3$; s) |
| I | (S→O)CH$_3$ | 4.25–4.39 ddd; J=3, 8.5&10Hz | 3.4–3.49 dd; J=3& 8.5Hz | 7.61, 7.8, &7.92 AROMATIC H's 2.75((S→O)CH$_3$; s) |
| I | S(O)$_2$CH$_3$ | 4.28–4.42 ddd; J=3, 8.5&9Hz | 3.44–3.52 dd; J=3& 8.5Hz | 7.92, 7.96&8.22 AROMATIC H's 3.08(S(O)$_2$CH$_3$; s) |
| I | CH$_2$OH | 4.22–4.36 ddd; J=3, | 3.38–3.46 dd; J=3& | 7.35, 7.6&7.69 AROMATIC H's |

TABLE XV

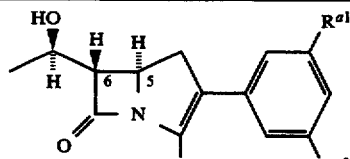

| $R^{a1}$ | $R^{a3}$ | UV (nm) $\lambda_{max}$ | $\epsilon_{ext}$ | NMR (D$_2$O) |
|---|---|---|---|---|
| I | SCH$_3$ | 303 | 7285 | 3.44–3.52(H6; dd; J=3&6H 2.43(SCH$_3$s); 7.23; 7.48& 7.53(AROMATIC H's) |
| I | (S→O)CH$_3$ | 307 | 9274 | 3.48–3.56(H6; dd; J=3&6Hz) 2.84((S→O)CH$_3$; s)7.62, 7.91& 7.95(AROMATIC H's) |
| I | S(O)$_2$CH$_3$ | 307 | 7186 | 3.5–3.56(H6; dd; J=3&6Hz) 3.22((S)$_2$CH$_3$; s)7.88; 8.06&8.2(AROMATIC H's) |
| I | CHO | 295 | 7579 | 3.5–3.56(H6; dd; J=3&6Hz) 3.22((S)$_2$CH$_3$; s)7.88; 8.06&8.82(AROMATIC H'S) |

TABLE XVI

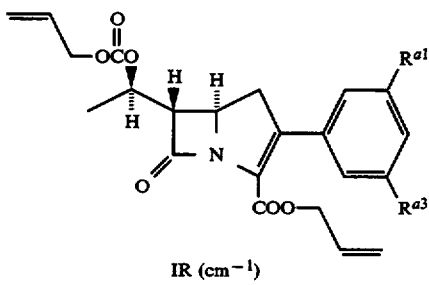

IR (cm$^{-1}$)

| | | (C=O) | | |
|---|---|---|---|---|
| $R^{a1}$ | $R^{a3}$ | B-LACTAM | CARBONATE | ESTER |
| SCH$_3$ | CH$_2$OH | 1780 | 1745 3500(OH) | 1725 |
| SCH$_3$ | CHO | 1780 | 1745 1705(CHO) | 1725 |
| (S→O)CH$_3$ | CH$_2$OH | 1780 | 1745 3430(OH) | 1725 |
| (S→O)CH$_3$ | CHO | 1785 | 1750 1710(CHO) | 1730 |
| S(O)$_2$CH$_3$ | CH$_2$OH | 1780 | 1745 3520(OH) | 1725 |
| S(O)$_2$CH$_3$ | CHO | 1785 | 1745 1705(CHO) | 1725 |

TABLE XVII

| | | NMR | | |
|---|---|---|---|---|
| $R^{a1}$ | $R^{a3}$ | $H_5$ | $H_6$ | $H_{2'}$–$H_{6'}$ |
| SCH$_3$ | CH$_2$OH | 4.22–4.36 ddd; J=3, 8.5 &9Hz | 3.38–3.48 dd; J=3& 8.5Hz | 7.1, 7.26&7.16Hz AROMATIC H's 2.48(SCH$_3$; s) |
| SCH$_3$ | CHO | 4.18–4.32 ddd; J=3, 8.5 &9.5Hz | 3.34–4.02 dd; J=3& 8.5Hz | 7.41, 7.51&7.61 AROMATIC H's 9.88(CHO; s) 2.46(SCH$_3$; s) |
| (S→O)Me | CH$_2$OH | 4.25–4.39 ddd; J=3, 8.5 &9.5Hz | 3.42–3.5 dd; J=3& 8.5Hz | 7.5, 7.57&7.62Hz AROMATIC H's 2.74((S→O)Me; s) |
| (S→O)Me | CHO | 4.30–4.43 ddd; J=3, 9 &10Hz | 3.45–3.56 dd; J=3& 9Hz | 7.99, 8.02&8.5Hz AROMATIC H's 2.82((S→O)Me; s) 10.06(CHO; s) |
| S(O)$_2$Me | CH$_2$OH | 4.27–4.41 ddd; J=3, 8.5 9.5Hz | 3.43–3.57 dd; J=3& 8.5Hz | 7.66, 6.85&7.9Hz AROMATIC H's) 3.07 (S(O)$_2$Me; s) |
| S(O)$_2$Me | CHO | 4.32–4.45 ddd; J=3, 8.5 &9.5Hz | 3.45–3.56 dd; J=3& 8.5Hz | 8.16, 8.24&8.4Hz AROMATIC H's 3.14 (S(O)$_2$Me; s) 10.02(CHO) |

TABLE XVIII

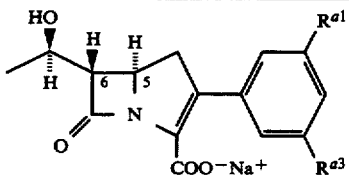

| | | UV (nm) | | |
|---|---|---|---|---|
| $R^{a1}$ | $R^{a3}$ | $\lambda_{max}$ | $\epsilon_{ext}$ | NMR (D$_2$O) |
| SCH$_3$ | CH$_2$OH | 303 | 9498 | 3.82–3.90(H6; dd; J=3&6Hz) 2.83(SCH$_3$; s); 7.46&7.57 (AROMATIC H's)4.94(CH$_2$O; s) |
| SCH$_3$ | CHO | 293 | 7823 | 3.92–3.98(H6; dd; J=3&6Hz) 2.84(SCH$_3$; s)7.86, 7.92& 8.01(AROMATIC H's)10.15(CHO; s) |
| (S→O)CH$_3$ | CH$_2$OH | 305 | 9675 | 3.78–3.88(H6; dd; J=3&6Hz) 3.18((S→O)CH$_3$; s)7.82, 7.91 (AROMATIC H's)5.0(CH$_2$O; s) |
| (S→O)CH$_3$ | CHO | 306 | 7700 | 3.85–3.94(H6; dd; J=3&6Hz)3.24 ((S→O)CH$_3$; s)8.26, 8.39, 8.46 (AROMATIC H's)10.3(CHO; s) |
| S(O)$_2$CH$_3$ | CH$_2$OH | 305 | 7415 | 3.85–3.93(H6; dd; J=3&5.5Hz) 3.60(S(O)$_2$CH$_3$; s)8.02, 8.18 (AROMATIC H's)5.08(CH$_2$O; s) |
| S(O)$_2$CH$_3$ | CHO | 309 | 7539 | 3.9–3.97(H6; dd; J=3&6Hz) 3.65(S(O)$_2$CH$_3$; s)8.55, 8.7 (AROMATIC H's)10.34(CHO; s) |

TABLE XIX

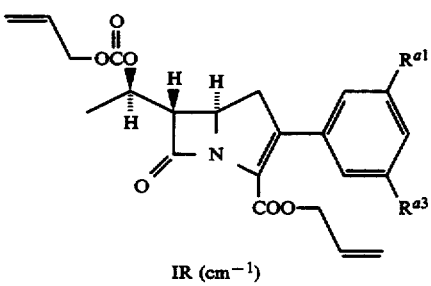

IR (cm$^{-1}$)

| $R^{a1}$ | $R^{a3}$ | (C=O) β-LACTAM | CARBONATE | ESTER |
|---|---|---|---|---|
| SCH$_3$ | SCH$_3$ | 1780 | 1745 | 1725 |
| SCH$_3$ | S→OCH$_3$ | 1785 | 1745 | 1725 |
| (S→O)CH$_3$ | S→OCH$_3$ | 1780 | 1745 | 1725 |
| (S→O)CH$_3$ | S(O)$_2$CH$_3$ | 1790 | 1750 | 1725 |
| S(O)$_2$CH$_3$ | S(O)$_2$CH$_3$ | 1785 | 1750 | 1725 |

TABLE XX

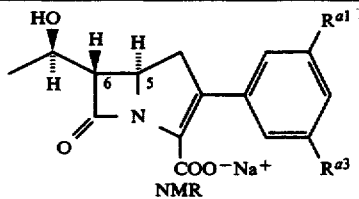

NMR

| $R^{a1}$ | $R^{a3}$ | H$_5$ | H$_5$ | H$_{2'}$–H$_{6'}$ |
|---|---|---|---|---|
| SCH$_3$ | SCH$_3$ | 4.24–4.38 ddd; J=3.9 &10Hz | 3.4–3.48 dd; J=3& 9Hz | 7.0&7.08, AROMATIC H's 2.47.(SCH$_3$; s) |
| SCH$_3$ | (S→O)CH$_3$ | 4.26–4.38 ddd; J=3, 9&9Hz | 3.42–3.48 dd: J=3& 9Hz | 7.36&7.48, AROMATIC H's 2.54(SCH$_3$; s) 2.76((S→O)CH$_3$; s) |
| (S→O)CH$_3$ | S(O)$_2$CH$_3$ | 4.28–4.42 ddd; J=3,9 &10Hz | 3.43–3.51 dd; J=3& 9Hz | 7.83&7.85 AROMATIC H's 2.80&2.82 ((S→O)CH$_3$; s) |
| (S→O)CH$_3$ | S(O)$_2$CH$_3$ | 4.3–4.44 ddd; J=3,9 &10Hz | 3.46–3.53 dd; J=3& 9Hz | 7.99, 8.08&8.12 AROMATIC H's 2.82((S→O)CH$_3$; s) 3.12(S(O)$_2$CH$_3$; s) |
| S(O)$_2$CH$_3$ | S(O)$_2$CH$_3$ | 4.32–4.46 ddd; J=3, 8.5&10Hz | 3.48–3.58 dd; J=3& 8.5Hz | 8.22&8.44 AROMATIC H's 3.14–3.54 (S(O)$_2$CH$_3$; s) |

TABLE XXI

| $R^{a1}$ | $R^{a3}$ | UV(nm) $\lambda_{max}$ | $\epsilon_{ext}$ | NMR(D$_2$O) |
|---|---|---|---|---|
| SCH$_3$ | SCH$_3$ | 303 | 5112 | 3.72–3.78 (H6; dd; J=3&6Hz) 7.28&7.38 (AROMATIC H's) 2.72(SCH$_3$; s) |
| SCH$_3$ | (S→O)CH$_3$ | 305 | 6341 | 3.80–3.87 (H6; dd; J=3&6Hz) 7.69, 7.75&7.8 (AROMATIC H's) 2.84(SCH$_3$; s) 3.18((S→O)CH$_3$; s) |
| (S→O)CH$_3$ | (S→O)CH$_3$ | 310 | 8669 | 3.84–3.90 (H6; dd; J=3&6Hz) 8.12&8.24 (AROMATIC H's) 3.22((S→O)CH$_3$; s) |
| (S→O)CH$_3$ | S(O)$_2$CH$_3$ | 310 | 9027 | 3.86–3.93 (H6; dd; J=3&6Hz) 8.28, 8.4&8.45 (AROMATIC H's) 3.23((S→O)CH$_3$; s) 3.61(S(O)$_2$CH$_3$; s) |
| S(O)$_2$CH$_3$ | S(O)$_2$CH$_3$ | 312 | 6788 | 3.82–3.90 (H6; dd; J=3&5.5Hz) 8.51&8.64 (AROMATIC H's) 3.59(S(O)$_2$CH$_3$; s) |

BIOLOGICAL DATA

The activity of the following compounds was measured against a strain of MRSA pathogen and reported as relative to the effectiveness of thienamycin, which is arbitrarily assigned an effectiveness of 1. Regarding this measure of activity, reference is made to R. Guthikonda, et al., J. Med. Chem., 30, 871 (1987).

TABLE XIII

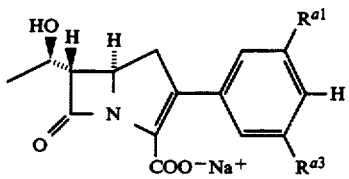

| $R^{a1}$ | $R^{a2}$ | $R^{a3}$ | ANTI-INFECTIVE ACTIVITY MRSA |
|---|---|---|---|
| I | H | H | 21 |
| H | I | H | 1.8 |
| I | H | I | 88 |
| Br | H | $CH_2OH$ | 8.7 |
| Br | H | HC=O | 219 |
| H | H | $CH_2OH$ | 0.9 |
| H | H | HC=O | 3.3 |
| H | HC=O | H | 2 |
| I | H | SMe | 60 |
| I | H | (S→O)Me | 63 |
| I | H | $O_2SMe$ | 63 |
| SMe | H | SMe | 28 |
| SMe | H | (S→O)Me | 6.1 |
| (S→O)Me | H | (S→O)Me | 1.2 |
| (S→O)Me | H | $O_2SMe$ | 3.7 |
| $O_2SMe$ | H | $O_2SMe$ | 12 |
| SMe | H | $CH_2OH$ | 3.2 |
| SMe | H | HC=O | 61 |

What is claimed is:

1. A compound of the formula:

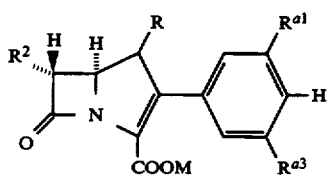

wherein:
R is H or $CH_3$;
$R^2$ is (R)—$CH_3CH(OH)$— or (R)—$CH_3CH(F)$—;
$R^{a1}$ is halogen, —$SCH_3$, —$S(O)_2CH_3$ and —(C=O)H;
$R^{a3}$ is halogen, —$SCH_3$, —$S(O)_2CH_3$, —(C=O)H, —(S→O)$CH_3$ and —cyano; and
M is a pharmaceutically acceptable cation or ester.

2. The compound of claim 1 wherein $R^2$ is and R is H.
3. The compound of claim 1 wherein halogen is selected from the group consisting of fluorine, chlorine, bromine and iodine.
4. The compound of claim 1 wherein M is a sodium or potassium cation.
5. A composition comprising a pharmaceutically acceptable carrier and from 0.1% to about 99% by weight of active material of claim 1.

6. A composition according to claim 5 which further comprises an inhibitorily effective amount of a DHP inhibitor.
7. A composition according to claim 6 wherein said DHP inhibitor is 7-(L-2-amino-2-carboxyethylthio)-2-(2,2-dimethylcyclopropanecarboxamide)-2-heptanoic acid.
8. A method for treating bacterial infection in mammals comprising administering a pharmaceutical composition comprising an effective amount of a compound of claim 1 and a pharmaceutically acceptable carrier therefor.
9. A method according to claim 8 which further comprises administering an inhibitorily effective amount of a DHP inhibitor.
10. A method according to claim 9 wherein said DHP inhibitor is 7-(L-2-amino-2-carboxyethylthio)-2-(2,2-dimethylcyclopropanecarboxamide)-2-heptanoic acid.
11. A compound of the formula:

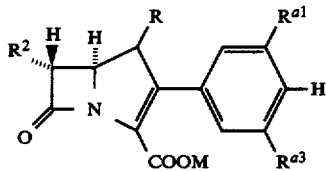

wherein $R^{a1}$ and $R^{a3}$ are simultaneously selected from the pairs of the group consisting of:

| $R^{a1}$ | $R^{a3}$ |
|---|---|
| F | F |
| Cl | Cl |
| Br | Br |
| Br | Cl |
| I | I |
| I | Br |
| I | Cl |
| Br | HC=O |
| I | HC=O |
| Br | SMe |
| Br | (S→O)Me |
| Br | $S(O)_2Me$ |
| I | SMe |
| I | (S→O)Me |
| I | $S(O)_2Me$ |
| SMe | SMe |
| SMe | (S→O)Me |
| (S→O)Me | $S(O)_2Me$ |
| $S(O)_2Me$ | $S(O)_2Me$ |
| SMe | HC=O |
| (S→O)Me | HC=O |
| $S(O)_2Me$ | HC=O |
| I | CN |
| HC=O | CN |
| (S→O)Me | CN and |
| $S(O)_2Me$ | CN. |

12. A compound of the formula I:

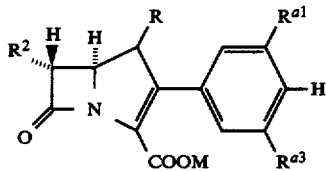

or a pharmaceutically acceptable salt or solvate thereof, wherein:
R is hydrogen or methyl;
$R^2$ is (R)$CH_3CH(OH)$— or (R)$CH_3CH(F)$—;
$R^{a1}$ and $R^{a3}$ are independently Cl, Br, F, I, —$SCH_3$, —$CH_2OH$, —$S(O)CH_3$, —$SO_2CH_3$ or —CHO; and
M is a cation or an ester forming group.

* * * * *

UNITED STATES PATENT AND TRADEMARK OFFICE
CERTIFICATE OF CORRECTION

PATENT NO. : 5,334,590
DATED : August 2, 1994
INVENTOR(S) : Frank DiNinno and Ravindra N. Guthikonda It is certified that error appears in the above-indentified patent and that said Letters Patent is hereby corrected as shown below:

In Claim 2, at column 33, line 60, between the words "is" and "and", please insert the functional groups -- (R)-CH3CH(OH)- --.

Signed and Sealed this

Twentieth Day of December, 1994

Attest:

BRUCE LEHMAN

*Attesting Officer*      *Commissioner of Patents and Trademarks*